US009193782B2

(12) United States Patent
Trieu et al.

(10) Patent No.: US 9,193,782 B2
(45) Date of Patent: Nov. 24, 2015

(54) USE OF THE SPARC MICROENVIRONMENT SIGNATURE IN THE TREATMENT OF CANCER

(75) Inventors: Vuong Trieu, Agoura Hills, CA (US); Xiping Liu, Temple City, CA (US); Neil Desai, Los Angeles, CA (US)

(73) Assignee: Abraxis BioScience, LLC, Los Angeles, CA (US)

( * ) Notice: Subject to any disclaimer, the term of this patent is extended or adjusted under 35 U.S.C. 154(b) by 1082 days.

(21) Appl. No.: 13/153,187

(22) Filed: Jun. 3, 2011

(65) Prior Publication Data
US 2012/0020959 A1 Jan. 26, 2012

Related U.S. Application Data

(60) Provisional application No. 61/351,233, filed on Jun. 3, 2010.

(51) Int. Cl.
| A61K 39/395 | (2006.01) |
| A61K 38/38 | (2006.01) |
| G01N 33/53 | (2006.01) |
| G01N 33/567 | (2006.01) |
| G01N 33/574 | (2006.01) |
| G01N 33/577 | (2006.01) |
| A61P 35/00 | (2006.01) |
| A61K 31/337 | (2006.01) |
| C40B 30/04 | (2006.01) |
| C07K 16/18 | (2006.01) |
| G01N 33/68 | (2006.01) |
| A61K 39/00 | (2006.01) |

(52) U.S. Cl.
CPC ............ *C07K 16/18* (2013.01); *G01N 33/6887* (2013.01); *A61K 2039/505* (2013.01); *G01N 2333/47* (2013.01); *G01N 2800/52* (2013.01)

(58) Field of Classification Search
None
See application file for complete search history.

(56) References Cited

U.S. PATENT DOCUMENTS

| 4,816,567 | A | 3/1989 | Cabilly et al. |
| 5,003,621 | A | 3/1991 | Gailus |
| 5,821,337 | A | 10/1998 | Carter et al. |
| 8,383,358 | B2 * | 2/2013 | Trieu et al. ............... 435/7.23 |
| 2007/0054271 | A1 | 3/2007 | Polyak et al. |
| 2008/0255035 | A1 | 10/2008 | Trieu et al. |
| 2009/0098210 | A1 | 4/2009 | Desai et al. |
| 2010/0069298 | A1 | 3/2010 | Penny et al. |

FOREIGN PATENT DOCUMENTS

| CN | 1867679 A | 11/2006 |
| CN | 1922332 A | 2/2007 |
| CN | 101014720 A | 8/2007 |
| CN | 101160321 A | 4/2008 |
| CN | 101454673 A | 6/2009 |
| CN | 101472943 A | 7/2009 |
| JP | 2007-531500 A | 11/2007 |
| JP | 2008-530248 A | 8/2008 |
| JP | 2009-536816 A | 10/2009 |
| WO | WO 2006/043362 A1 | 4/2006 |
| WO | WO 2008/060651 A2 | 5/2008 |
| WO | WO 2008/076373 A1 | 6/2008 |
| WO | WO 2008/109996 A1 | 9/2008 |
| WO | WO 2008/128169 A1 | 10/2008 |
| WO | WO 2008/150532 A1 | 12/2008 |
| WO | 2010/138839 A2 | 12/2010 |
| WO | 2011/035274 A1 | 3/2011 |

OTHER PUBLICATIONS

R&D Systems, Cat. No. AF941, downloaded from the web Dec. 22, 2014.*
R&D Systems, Cat. No. Mab941, downloaded from the web Dec. 22, 2014.*
Desai et al., Abstract 1004, *Ep. J. Cancer*, 7(2), Supp., p. 88 (Sep. 1, 2009).
Desai et al., Abstract PP73, *Ep. J. Cancer*, 7(4), Supp., p. 16 (Oct. 1, 2009).
European Patent Application 11790502.6, Search Report (Mar. 7, 2014).
Beck et al., *Laboratory Investigation*, 88, 591-601 (2008).
Infante et al., *J. Clin. Oncol.*, 25(3), 319-325 (Jan. 20, 2007).
Massi et al., *Human Pathology*, 30(3), 339-344 (Mar. 1999).
Watkins et al., *Prostaglandins Leukot. Essent. Fatty Acids*, 72, 267-272 (2005).
European Patent Application No. 10817999.5, Search Report (Aug. 13, 2013).
Sato et al., *Oncogene*, 22, 5021-5030 (2003).
Chinese Patent Application No. 201180034954.9, Search Report (Feb. 8, 2014).
Bellahcene et al., *Am. J. Path.*, 146(1), 95-100 (Jan. 1995).
Bradshaw et al., *PNAS*, 100(10), 6045-6050 (May 13, 2003).
Chlenski et al., *Cancer Res.*, 62, 7357-7363 (Dec. 15, 2002).
Desai et al., *Translational Oncology*, 2(2), 59-64 (Jun. 2009).
Dhanesuan et al., *Br. Cancer Res. and Treatment*, 75, 73-85 (2002).
Harlow, Ed and David Lane, *Using Antibodies: A Laboratory Manual*, Chapter 11, "Epitope Mapping," pp. 379-405 Cold Spring Harbor Laboratory Press, Cold Spring Harbor, NY (1999).
Kim et al., *J. Korean Med. Sci.*, 13, 652-657 (1998).
Lane et al., *FASEB J.*, 8, 163-173 (1994).
Mason et al., *EMBO J.*, 5(7), 1465-1472 (1986).
Porter et al. *J. Histochem. & Cytochem.*, 43(8), 791-800 (1995).
Rempel et al., *Clin. Cancer Res.*, 5, 237-241 (Feb. 1999).
Swaroop et al., *Genomics*, 2, 37-47 (1988).
Yamanaka et al., *J. Urology*, 166, 2495-2499 (Dec. 2001).
Yan et al., *J. Histochem. & Cytochem.*, 47(12), 1495-1505 (1999).
Yiu et al., *Am. J. Path.*, 159(2), 609-622 (Aug. 2001).
Australian Patent Application No. 2010295324, search report (Jun. 20, 2014).
Sweetwyne et al., *J. Histochem. & Cytochem.*, 52(6), 723-733 (2004).
Tai et al., *J. Clin. Invest.*, 115(6), 1492-1502 (Jun. 2005).
Chinese Patent Application No. 201080047076.X, Office Action (Jul. 7, 2014).
Japanese Patent Application No. 529971/2012, Office Action (Oct. 7, 2014).
Japanese Patent Application No. 529971/2012, Search Report (Jul. 21, 2015).
Matsubayashi et al., *Journal of the Japan Pancreas Society*, 22(3), 236 (May 2007).
Yardley et al., *J. Clin. Oncol.*, 28(15) Supp., 10574 (May 20, 2010).
Japanese Patent Application No. 513391/2013, Search Report (May 12, 2015).

* cited by examiner

*Primary Examiner* — Karen Canella
(74) *Attorney, Agent, or Firm* — Leydig, Voit & Mayer, Ltd.

(57) ABSTRACT

The invention provides multiparametric anti-SPARC antibody-based techniques for predicting the response to chemotherapy.

6 Claims, 5 Drawing Sheets

A

B

C

A

B

C

USE OF THE SPARC MICROENVIRONMENT SIGNATURE IN THE TREATMENT OF CANCER

Figure 1:
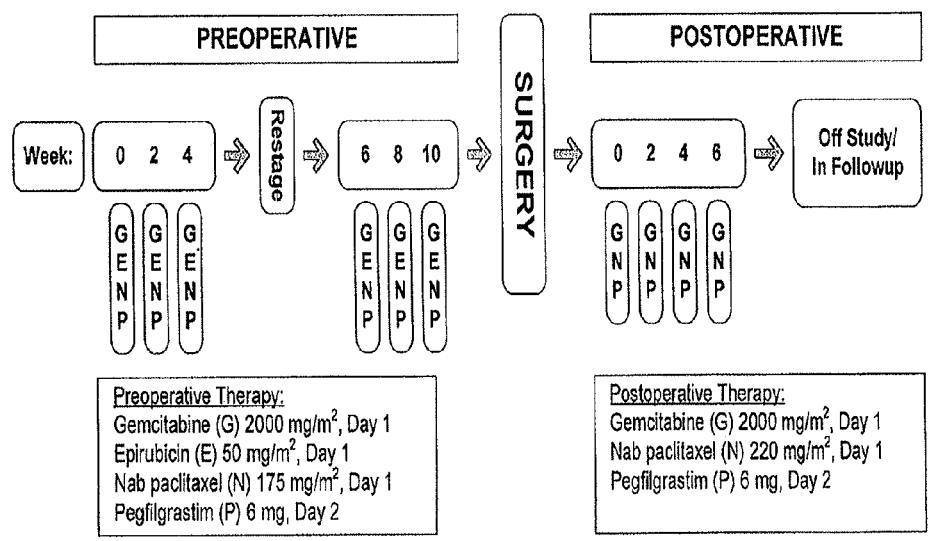

This application claims priority benefit under 35 U.S.C. §119(e) of U.S. Provisional Application No. 61/351,233 filed on Jun. 3, 2010 the entire contents of which are incorporated herein by reference.

BACKGROUND OF THE INVENTION

Secreted protein acidic and rich in cysteine (also known as osteonectin, BM40, or SPARC) (hereinafter "SPARC"), is a matrix-associated protein that elicits changes in cell shape, inhibits cell-cycle progression, and influences the synthesis of extracellular matrix (Bradshaw et al., Proc. Nat. Acad. Sci. USA 100: 6045-6050 (2003)). The murine SPARC gene was cloned in 1986 (Mason et al., EMBO J. 5: 1465-1472 (1986)) and a full-length human SPARC cDNA was cloned and sequenced in 1987 (Swaroop et al., Genomics 2: 37-47 (1988)). SPARC expression is developmentally regulated, and is predominantly expressed in tissues undergoing remodeling during normal development or in response to injury. For example, high levels of SPARC protein are expressed in developing bones and teeth (see, e.g., Lane et al., FASEB J., 8, 163 173 (1994); Yan & Sage, J. Histochem. Cytochem. 47:1495-1505 (1999)).

SPARC is upregulated in several aggressive cancers, but is absent in the corresponding normal tissues (Porter et al., J. Histochem. Cytochem., 43, 791 (1995)). SPARC expression is induced among a variety of tumors (e.g., bladder, liver, ovary, kidney, gut, and breast). In bladder cancer, for example, SPARC expression has been associated with advanced carcinoma. Invasive bladder tumors of stage T2 or greater have been shown to express higher levels of SPARC relative to bladder tumors of stage T1 (or less superficial tumors), and a poorer prognosis (see, e.g., Yamanaka et al., J. Urology, 166, 2495 2499 (2001)). In meningiomas, SPARC expression has been associated only with invasive tumors (see, e.g., Rempel et al., Clincal Cancer Res., 5, 237 241 (1999)). SPARC expression also has been detected in 74.5% of in situ invasive breast carcinoma lesions (see, e.g., Bellahcene, et al., Am. J. Pathol., 146, 95 100 (1995)), and 54.2% of infiltrating ductal carcinoma of the breast (see, e.g., Kim et al., J. Korean Med. Sci., 13, 652 657 (1998)). SPARC expression also has been associated with frequent microcalcification in breast cancer (see, e.g., Bellahcene et al., supra), suggesting that SPARC expression may be responsible for the affinity of breast metastases for the bone.

Surprisingly, SPARC has also been shown to have anti-tumor activity in some systems. SPARC is a potent cell cycle inhibitor that arrests cells in mid-G (Yan & Sage, J. Histochem. Cytochem. 47:1495-1505 (1999)) and the inducible expression of SPARC has been shown to inhibit breast cancer cell proliferation in an in vitro model system (Dhanesuan et al., Breast Cancer Res. Treat. 75:73-85 (2002)). Similarly, exogenous SPARC can reduce the proliferation of both HOSE (human ovarian surface epithelial) and ovarian cancer cells in a concentration-dependent manner. In addition, SPARC induces apoptosis in ovarian cancer cells. Further evidence for SPARC receptors present on cells such as ovarian epithelial cells has been reported. It has been proposed that the binding of SPARC to its receptor is likely to trigger tissue-specific signaling pathways that mediate its tumor suppressing functions (Yiu et al., Am. J. Pathol. 159:609-622 (2001)). Purified SPARC has also been reported to potently inhibit angiogenesis and significantly impair neuroblastoma tumor growth in an in vivo xenograft model system (Chlenski et al., Cancer Res. 62:7357-7363 (2002)).

Cancer is now primarily treated with one or a combination of three types of therapies: surgery, radiation, and chemotherapy. Surgery generally is only effective for treating the earlier stages of cancer. For more than 50% of individuals with cancer, by the time they are diagnosed they are no longer candidates for effective surgical treatment. Radiation therapy is only effective for individuals who present with clinically localized disease at early and middle stages of cancer, and is not effective for the late stages of cancer with metastasis.

Chemotherapy involves the disruption of cell replication or cell metabolism. Chemotherapy can be effective, but there are severe side effects, e.g., vomiting, low white blood cells (WBC), loss of hair, loss of weight and other toxic effects. Because of the extremely toxic side effects, many individuals with cancer cannot successfully finish a complete chemotherapy regime. Chemotherapy-induced side effects significantly impact the quality of life of the individual and may dramatically influence individual compliance with treatment. Additionally, adverse side effects associated with chemotherapeutic agents are generally the major dose-limiting toxicity (DLT) in the administration of these drugs. For example, mucositis is one of the major dose limiting toxicities for several anticancer agents, including the antimetabolite cytotoxic agents 5-FU, methotrexate, and antitumor antibiotics, such as doxorubicin. Many of these chemotherapy-induced side effects, if severe, may lead to hospitalization or require treatment with analgesics to manage pain. Some individuals with cancer die from the chemotherapy due to poor tolerance. The extreme side effects of anticancer drugs are caused by the poor target specificity of such drugs. The drugs circulate through most normal organs of individuals as well as intended target tumors. The poor target specificity that causes side effects also decreases the efficacy of chemotherapy because only a fraction of the drugs are correctly targeted. The efficacy of chemotherapy is further decreased by poor retention of the anti-cancer drugs within the target tumors.

Due to the severity and breadth of cancer, there is a great need for effective treatments of these diseases and disorders that overcome the shortcomings of surgery, chemotherapy, and radiation treatment. In particular, in view of the serious side effects associated with chemotherapy, there is a need to identify which tumors will or will not respond to chemotherapeutic regimens.

BRIEF SUMMARY OF THE INVENTION

The invention provides the "SPARC microenvironment signature" as a tool in the management of animals with cancer. The "SPARC microenvironment signature" (SMS) is the immunostaining pattern observed when histologic sections are stained with two anti-SPARC antibodies, a first anti-SPARC antibody which preferentially stains SPARC in tumor cells and a second anti-SPARC antibody, which preferentially stains SPARC in fibroblasts. To determine the SMS of the tumor cells, fibroblasts, inflammatory cells, acellular stroma/matrix, blood vessels, nerve tissue, normal anatomy within tumor or any combinations thereof are immunostained and scored (as percentage positive cells, percentage of the field immunostained at a given magnification and/or staining intensity from 0-4).

In one embodiment, the present invention provides methods of treating a tumor in an animal with a chemotherapeutic regimen comprising:
(a) preparing a plurality of histologic sections of the tumor to obtain SPARC microenvironment signature, (b) immunostaining a histologic section of the tumor with a first anti-SPARC antibody, wherein the first anti-SPARC antibody preferentially stains SPARC in tumor cells, (c) immunostaining a histologic section of the tumor with a second anti-SPARC antibody, wherein the second anti-SPARC antibody preferentially stains SPARC in fibroblasts, (d) determining the staining of the tumor cells, fibroblasts, inflammatory cells, acellular stroma/matrix, blood vessels, nerve tissue, normal anatomy within tumor or any combinations thereof with the first anti-SPARC antibody and the staining of the tumor cells, fibroblast, inflammatory cells, acellular stroma/matrix, blood vessels, nerve tissue, normal anatomy within tumor or any combinations thereof with the second antibody, and (e) administering a therapeutically effective amount of the chemotherapeutic regimen if a predefined SMS is demonstrated by the immunostaining. In another embodiment, the invention provides a method for predicting the response of a tumor in an animal to a chemotherapeutic regimen comprising:

(a) Preparing a plurality of histologic sections of the tumor to obtain SPARC microenvironment signature, (b) immunostaining a histologic section of the tumor with a first anti-SPARC antibody, wherein the first anti-SPARC antibody preferentially stains SPARC in tumor cells, (c) immunostaining a histologic section of the tumor with a second anti-SPARC antibody, wherein the second anti-SPARC antibody preferentially stains SPARC in fibroblasts, (d) determining the staining of the tumor cells, fibroblasts, inflammatory cells, acellular stroma/matrix, blood vessels, nerve tissue, normal anatomy within tumor or any combinations thereof with the first anti-SPARC antibody and the staining of the tumor cells, fibroblast, inflammatory cells, acellular stroma/matrix, blood vessels, nerve tissue, normal anatomy within tumor or any combinations thereof with the second antibody, and (e) predicting a positive response to the chemotherapeutic regimen if a predefined SMS is demonstrated by the immunostaining.

In another embodiment, the invention provides a method for predicting if an animal with a tumor has a low risk of the progression of that tumor or a low risk of death from the tumor comprising:

(a) Preparing a plurality of histologic sections of the tumor to obtain SPARC microenvironment signature, (b) immunostaining a histologic section of the tumor with a first anti-SPARC antibody, wherein the first anti-SPARC antibody preferentially stains SPARC in tumor cells, (c) immunostaining a histologic section of the tumor with a second anti-SPARC antibody, wherein the second anti-SPARC antibody preferentially stains SPARC in fibroblasts, (d) determining the staining of the tumor cells, fibroblasts, inflammatory cells, acellular stroma/matrix, blood vessels, nerve tissue, normal anatomy within tumor or any combinations thereof with the first anti-SPARC antibody and the staining of the tumor cells, fibroblast, inflammatory cells, acellular stroma/matrix, blood vessels, nerve tissue, normal anatomy within tumor or any combinations thereof with the second antibody, and (e) predicting a low risk of progression of the tumor or a low risk of death from the tumor if a predefined SMS is demonstrated by the immunostaining.

The invention also provides kits for predicting the response of a tumor in an animal to a chemotherapeutic regimen comprising:

(a) an immunostain with a first anti-SPARC antibody, wherein the first anti-SPARC antibody preferentially stains SPARC in tumor cells, and (b) an immunostain with a second anti-SPARC antibody, wherein the second anti-SPARC antibody preferentially stains SPARC in fibroblasts.

BRIEF DESCRIPTION OF THE SEVERAL VIEWS OF THE DRAWING(S)

FIG. 1 depicts a schematic representation of a clinical trial design.

Figure 2:
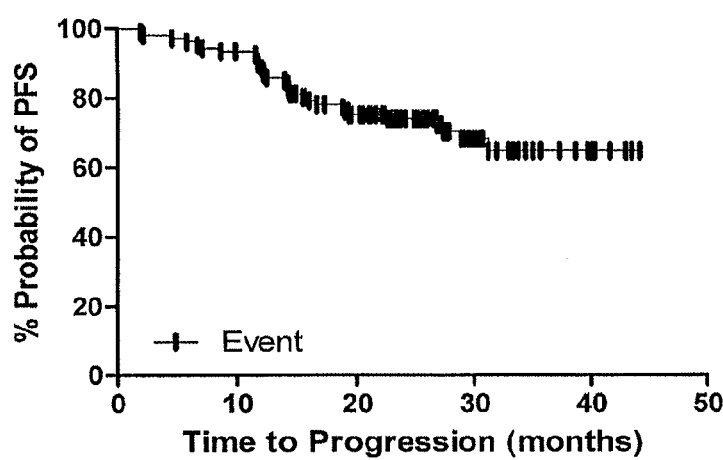
Figure 2:
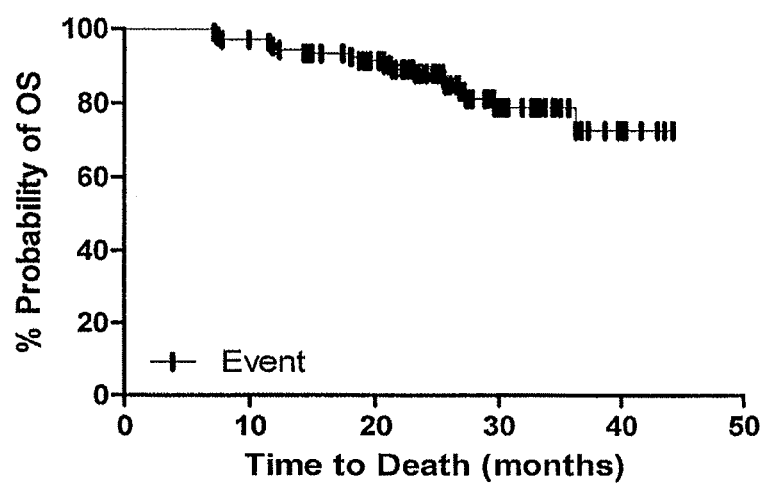

FIG. 2. graphically presents the outcomes for HER2-negative patients in the neoadjuvant breast cancer trial (N=107). FIG. 2A presents progression free survival (PFS) and FIG. 2B presents overall survival (OS). (Median PFS and OS have not been reached for this patient population.)

FIG. 3A-C graphically demonstrates that the addition of SMS risk clusters to other prognostic factors further discriminated tumors with low risk (0 risk factor), medium risk (1 risk factor), and high risk (2 risk factors) with regard to shortened PFS.

FIG. 4A-C graphically demonstrates that the addition of SMS risk clusters to other prognostic factors further discriminated tumors with low risk (0 risk factors), medium risk (1 risk factor), and high risk (2 risk factors) with regard to shortened OS.

DETAILED DESCRIPTION OF THE INVENTION

As used herein, the term "tumor" refers to any neoplastic growth, proliferation or cell mass whether benign or malignant (cancerous), whether a primary site lesion or metastases.

As used herein, the term "cancer" refers to a proliferative disorder caused or characterized by the proliferation of cells which have lost susceptibility to normal growth control. Cancers of the same tissue type usually originate in the same tissue, and may be divided into different subtypes based on their biological characteristics. Four general categories of cancers are carcinoma (epithelial tissue derived), sarcoma (connective tissue or mesodermal derived), leukemia (blood-forming tissue derived) and lymphoma (lymph tissue derived). Over 200 different types of cancers are known, and every organ and tissue of the body may be affected. Specific examples of cancers that do not limit the definition of cancer may include melanoma, leukemia, astrocytoma, glioblastoma, retinoblastoma, lymphoma, glioma, Hodgkins' lymphoma and chronic lymphocyte leukemia. Examples of organs and tissues that may be affected by various cancers include pancreas, breast, thyroid, ovary, uterus, testis, prostate, thyroid, pituitary gland, adrenal gland, kidney, stomach, esophagus or rectum, head and neck, bone, nervous system, skin, blood, nasopharyngeal tissue, lung, urinary tract, cervix, vagina, exocrine glands and endocrine glands. Alternatively, a cancer may be multicentric or of unknown primary site (CUPS).

As used herein, a 'cancerous cell' refers to a cell that has undergone a transformation event and whose growth is no longer regulated to the same extent as before said transformation event.

As used herein, a "medicament" is a composition capable of producing an effect that may be administered to a patient or test subject. The effect may be chemical, biological or physical, and the patient or test subject may be human, or a non-human animal, such as a rodent or transgenic mouse. The composition may include small organic or inorganic molecules with distinct molecular composition made synthetically, found in nature, or of partial synthetic origin. Included in this group are nucleotides, nucleic acids, amino acids, peptides, polypeptides, proteins, or complexes comprising at least one of these entities, The medicament may be comprised of the effective composition alone or in combination with a pharmaceutically acceptable excipient.

As used herein, a "pharmaceutically acceptable excipient" includes any and all solvents, dispersion media, coatings, antibacterial, antimicrobial or antifungal agents, isotonic and absorption delaying agents, and the like that are physiologically compatible. The excipient may be suitable for intravenous, intraperitoneal, intramuscular, intrathecal or oral administration. The excipient may include sterile aqueous solutions or dispersions for extemporaneous preparation of sterile injectable solutions or dispersion. Use of such media for preparation of medicaments is known in the art.

As used herein, a "pharmacologically effective amount" of a medicament refers to using an amount of a medicament present in such a concentration to result in a therapeutic level of drug delivered over the term that the drug is used. This may be dependent on mode of delivery, time period of the dosage, age, weight, general health, sex and diet of the subject receiving the medicament. The determination of what dose is a "pharmacologically effective amount" requires routine optimization which is within the capabilities of one of ordinary skill in the art. A cancer or cancerous cell may be described as "sensitive to" or "resistant to" a given therapeutic regimen or chemotherapeutic agent based on the ability of the regimen to kill cancer cells or decrease tumor size, reduce overall cancer growth (i.e. through reduction of angiogenesis), and/or inhibit metastasis. Cancer cells that are resistant to a therapeutic regimen may not respond to the regimen and may continue to proliferate. Cancer cells that are sensitive to a therapeutic regimen may respond to the regimen resulting in cell death, a reduction in tumor size, reduced overall growth (tumor burden) or inhibition of metastasis.

As used herein, a "therapeutic regimen" or "therapy" refers to the administration of at least one agent which is harmful to cancerous cells. Suitable therapeutic regimens for use in accordance with the invention include, but are not limited to, "chemotherapeutic regimens," "radiotherapeutic regimens," "alternative therapeutic regimen" and combinations thereof.

As used herein, "chemotherapy" refers to the administration of at least one chemotherapy agent which is harmful to destroy cancerous cells. There are a myriad of such chemotherapy agents available to a clinician. Chemotherapy agents may be administered to a subject in a single bolus dose, or may be administered in smaller doses over time. A single chemotherapeutic agent may be used (single-agent therapy) or more than one agent may be used in combination (combination therapy). Chemotherapy may be used alone to treat some types of cancer. Alternatively, chemotherapy may be used in combination with other types of treatment, for example, radiotherapy or alternative therapies (for example immunotherapy) as described herein. Additionally, a chemosensitizer may be administered as a combination therapy with a chemotherapy agent.

As used herein, a "chemotherapeutic agent" or "anticancer drug" refers to a medicament that may be used to treat cancer, and generally has the ability to kill cancerous cells directly.

Examples of chemotherapeutic agents include alkylating agents, antimetabolites, natural products, hormones and antagonists, and miscellaneous agents. Examples of alternate names are indicated in brackets. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-mercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interlelukin 2. Examples of hormones and antagonists include luteinising releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (cis-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib. Alternate names and trade-names of these and additional examples of chemotherapeutic agents, and their methods of use including dosing and administration regimens, will be known to a person versed in the art. In particular, suitable chemotherapeutic agents for use in accordance with the invention include, without limitation, nanoparticle albumin-bound paclitaxels.

Abraxane™, also known as ABI-007, is a preferred chemotherapeutic agent. Abraxane™ is an albumin-nanoparticle formulation of paclitaxel. The use of an albumin nanoparticle as a vehicle results in the formation of a colloid when reconstituted with saline. Based on clinical studies, it has been shown that the use of Abraxane™ is characterized by reduced hypersensitivity reactions as compared with Taxol.™ Accordingly, premedication is not required for patients receiving Abraxane™.

Another advantage of the albumin-nanoparticle formulation is that by excluding toxic emulsifiers it is possible to administer higher doses of paclitaxel at more frequent intervals than is possible with Taxol™. The potential exists that enhanced efficacy could be seen in solid tumors as a consequence of (i) higher tolerable doses (300 mg/m²), (ii) longer half-life, (iii) prolonged local tumor availability and/or (iv) sustained in vivo release Abraxane™.

A positive response is defined as including, but not limited, to pathological response (reduction in tumor size or burden), overall survival, or progression free survival as shown by an improvement of the metric by at least 5%, preferably by at least 10%, more preferably by at least 15%, even more preferably by at least 20%, most preferably by at least 25% or more. Alternatively, the metric shows an improvement by a statistically significant amount in comparison with no or prior or alternative therapy.

A negative response includes, but is not limited to pathological progression, decreased overall or progression free survival.

As used herein, the term "radiotherapeutic regimen" or "radiotherapy" refers to the administration of radiation to kill cancerous cells. Radiation interacts with various molecules within the cell, but the primary target, which results in cell death is the deoxyribonucleic acid (DNA). However, radiotherapy often also results in damage to the cellular and nuclear membranes and other organelles. DNA damage usually involves single and double strand breaks in the sugar-phosphate backbone. Furthermore, there can be cross-linking of DNA and proteins, which can disrupt cell function. Depending on the radiation type, the mechanism of DNA damage may vary as does the relative biologic effectiveness. For example, heavy particles (i.e. protons, neutrons) damage DNA directly and have a greater relative biologic effectiveness. Electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray.

Radiotherapy may further be used in combination chemotherapy, with the chemotherapeutic agent acting as a radiosensitizer. The specific choice of radiotherapy suited to an individual patient may be determined by a skilled person at the point of care, taking into consideration the tissue and stage of the cancer.

As used herein, the term "alternative therapeutic regimen" or "alternative therapy" may include for example, biologic response modifiers (including polypeptide-, carbohydrate-, and lipid-biologic response modifiers), toxins, lectins, anti-angiogenic agents, receptor tyrosine kinase inhibitors (for example Iressa™ (gefitinib), Tarceva™ (erlotinib), Erbitux™ (cetuximab), imatinib mesilate (Gleevec™)), proteosome inhibitors (for example bortezomib (Velcade™)); VEGFR2 inhibitors such as PTK787 (ZK222584), aurora kinase inhibitors (for example ZM447439); mammalian target of rapamycin (mTOR) inhibitors, cyclooxygenase-2 (COX-2) inhibitors, rapamycin inhibitors (for example sirolimus (Rapamune™)); farnesyltransferase inhibitors (for example tipifarnib (Zarnestra™)); matrix metalloproteinase inhibitors (for example BAY 12-9566; sulfated polysaccharide tecogalan); angiogenesis inhibitors (for example bevacizumab (Avastin™)); analogues of fumagillin such as TNP-4; carboxyaminotriazole; BB-94 and BB-2516; thalidomide; interleukin-12; linomide; peptide fragments; and antibodies to vascular growth factors and vascular growth factor receptors); platelet derived growth factor receptor inhibitors, protein kinase C inhibitors, mitogen-activated kinase inhibitors, mitogen-activated protein kinase inhibitors, Rous sarcoma virus transforming oncogene (SRC) inhibitors, histonedeacetylase inhibitors, small hypoxia-inducible factor inhibitors, hedgehog inhibitors, and TGF-β signaling inhibitors. Furthermore, an immunotherapeutic agent would also be considered an alternative therapeutic regimen. Examples include chemokines, chemotaxins, cytokines, interleukins, or tissue factor. Suitable immunotherapeutic agents also include serum or gamma globulin containing preformed antibodies; nonspecific immunostimulating adjuvants; active specific immunotherapy; and adoptive immunotherapy. In addition, alternative therapies may include other biological-based chemical entities such as polynucleotides, including antisense molecules, polypeptides, antibodies, gene therapy vectors and the like. Such alternative therapeutics may be administered alone or in combination, or in combination with other therapeutic regimens described herein. Alternate names and trade-names of these agents used in alternative therapeutic regimens and additional examples of agents used in alternative therapeutic regimens, and their methods of use including dosing and administration regimens, will be known to a physician versed in the art. Furthermore, methods of use of chemotherapeutic agents and other agents used in alternative therapeutic regimens in combination therapies, including dosing and administration regimens, will also be known to a person versed in the art.

In particular, suitable alternative therapeutic regimens include, without limitation, antibodies to molecules on the surface of cancer cells such as antibodies to Her2 (e.g., trastuzumab), EGF or EGF Receptors, VEGF (e.g., bevacizumab) or VEGF Receptors, CD20, and the like. The therapeutic agent may further comprise any antibody or antibody fragment which mediates one or more of complement activation, cell mediated cytotoxicity, inducing apoptosis, inducing cell death, and opsonization. For example, such an antibody fragment may be a complete or partial Fc domain.

As used herein, the term "histologic section" refers to a thin section of a tissue sample suitable for mounting on a microscope slide and staining with any suitable protocol. As used herein, "immunostaining a histologic section" refers to the staining of the cells and intracellular matrix of the histologic section resulting from the binding of antibodies to components of the cells are intracellular matrix. As used herein, to "predominantly" or "preferentially" stain a structure, e.g., a cancer cell over a fibroblast, the immunostaining of the preferentially stained structure in the histologic section should be of an intensity graded by a pathologist by any suitable system, including, e.g., 3/3 when observed microscopically by those of ordinary skill, well all other structures stain with only an intensity of 1/3 or show 0/3 (no staining).

As used herein, the term "epitope" refers to the three-dimensional structure bound by an antibody, and in particular the amino acid sequence targeted by the antibody. As used herein, the term "epitope recognized by the MAB941 monoclonal antibody" refers to the amino acid sequence in SPARC bound by the MAB941 monoclonal anybody. (SPARC monoclonal antibody (R&D Systems, Minneapolis, Minn.), catalog #MAB941)

As used herein, "immunodominant epitopes" refers to the three-dimensional structures bound with the greatest collective avidity by the antibodies in polyclonal antisera. In particular, the epitopes responsible for the pattern of staining in immunostaining protocol employing that polyclonal antisera. As used herein, the term "immunodominant SPARC epitopes recognized by the AF941 polyclonal antibody refers" to the SPARC peptides and amino acid sequences found with the greatest avidity by the AF941 polyclonal antisera. Accordingly, binding to and staining of these SPARC peptides and amino acid sequences results and the majority of immunostaining observed. (SPARC polyclonal antibody (R&D Systems, Minneapolis, Minn.), catalog #AF941).

Epitope mapping can also be done using standard techniques known in the art. For example, the protocols from "Epitope Mapping," Chapter 11, in Using Antibodies by Ed Harlow and David Lane. Cold Spring Harbor Laboratory Press, Cold Spring Harbor, N.Y., USA, 1999, which are hereby incorporated by reference in their entirety. By mapping the epitopes, epitope-specific antibodies can be readily generated by standard techniques.

By "antibodies" it is meant without limitation, monoclonal antibodies, polyclonal antibodies, dimers, multimers, multispecific antibodies (e.g., bispecific antibodies). Antibodies may be murine, human, humanized, chimeric, or derived from other species. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody.

An antibody includes a full-length immunoglobulin molecule or an immunologically active portion of a full-length immunoglobulin molecule, i.e., a molecule that contains an antigen binding site that immunospecifically binds an antigen of a target of interest or part thereof. Targets include, cancer cells or other cells that produce autoimmune antibodies associated with an autoimmune disease.

The immunoglobulins disclosed herein can be of any class (e.g., IgG, IgE, IgM, IgD, and IgA) or subclass (e.g., IgG1, IgG2, IgG3, IgG4, IgA1 and IgA2) of immunoglobulin molecule. The immunoglobulins can be derived from any species.

"Antibody fragments" comprise a portion of a full length antibody, which maintain the desired biological activity. "Antibody fragments" are generally the antigen binding or variable region thereof. Examples of antibody fragments include Fab, Fab', F(ab')2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The monoclonal antibodies referenced herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567). Chimeric antibodies of interest herein include "primatized" antibodies comprising variable domain antigen-binding sequences derived from a non-human primate (e.g., Old World Monkey or Ape) and human constant region sequences.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express Fc.γ.RIII only, whereas monocytes express FcγRI, FcγRII and FcγRIII. To assess ADCC activity of a molecule of interest, an in vitro ADCC assay may be performed (U.S. Pat. No. 5,003,621; U.S. Pat. No. 5,821,337). Useful effector cells for such assays include peripheral blood mononuclear cells (PBMC) and Natural Killer (NK) cells.

An antibody which "induces cell death" is one which causes a viable cell to become nonviable. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue or 7AAD can be assessed relative to untreated cells. Cell death-inducing antibodies are those which induce PI uptake in the PI uptake assay in BT474 cells.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies).

As used herein, a "chemosensitizer" or "sensitizer" is a medicament that may enhance the therapeutic effect of a chemotherapeutic agent, radiotherapy treatment or alternative therapeutic regimen, and therefore improve efficacy of such treatment or agent. The sensitivity or resistance of a tumor or cancerous cell to treatment may also be measured in an animal, such as a human or rodent, by, e.g., measuring the tumor size, tumor burden or incidence of metastases over a period of time. For example, about 2, about 3, about 4 or about 6 months for a human and about 2-4, about 3-5, or about 4-6 weeks for a mouse. A composition or a method of treatment may sensitize a tumor or cancerous cell's response to a therapeutic treatment if the increase in treatment sensitivity or the reduction in resistance is about 10% or more, for example, about 30%, about 40%, about 50%, about 60%, about 70%, about 80%, or more, to about 2-fold, about 3-fold, about 4-fold, about 5-fold, about 10-fold, about 15-fold, about 20-fold or more, compared to treatment sensitivity or resistance in the absence of such composition or method. The determination of sensitivity or resistance to a therapeutic treatment is routine in the art and within the skill of a person versed in the art.

The terms "'peptide," "polypeptide," and "protein" may be used interchangeably, and refer to a compound comprised of at least two amino acid residues covalently linked by peptide bonds or modified peptide bonds, for example peptide isosteres (modified peptide bonds) that may provide additional desired properties to the peptide, such as increased half-life. A peptide may comprise at least two amino acids. The amino acids comprising a peptide or protein described herein may also be modified either by natural processes, such as post-translational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

The methodology for determining the SPARC Microenvironment Signature (SMS) comprises immunostaining histologic sections of the tumor with a first anti-SPARC antibody, wherein the first anti-SPARC antibody preferentially stains SPARC in tumor cells and with a second anti-SPARC antibody, wherein the second anti-SPARC antibody preferentially stains SPARC in fibroblasts. Seven components of SPARC expression were determined with the two different antibodies: tumor cells, fibroblasts, inflammatory cells, acellular stroma/matrix (stroma), blood vessels, nerves and the other normal anatomy within the tumor. The percent of cells stained in each field, the intensity of staining (from 0-4) and an overall score (dependant variable) for each of the components of the tumor was determined (total variables per patient: 7 components×2 antibodies×3 scores=42 variables scored.)

In all methods of the present invention, suitable anti-SPARC antibodies can be identified using any suitable method known to one of ordinary skill in the art, such as tissue microarrays, to assay for the correct distribution of tumor and fibroblast SPARC staining. Mono and polyclonal antibodies made by standard techniques known in the art can be used. One particularly preferred anti-SPARC antibody is an antibody that recognizes the immunodominant epitopes recognized by the AF941 polyclonal antibody, which can be used to preferentially immunostain tumor cells.

Tissue microarrays comprising duplicate 0.6-mm cores from the selected blocks can be constructed using a Beecher Instruments Micro Tissue Arrayer. Four-micrometer-thick sections can be cut from completed array blocks and transferred to silanized glass slides. Sections from these arrays then can be stained with hematoxylin and eosin to assess adequacy. Microwave antigen retrieval can consist of placing the slides in 10 mm citrate buffer (pH 6.0) in a pressure cooker (Nordic Ware) and microwaving on high power until the buffer has boiled under pressure for 4 minutes. At this point, microwaving is stopped and the slides are incubated in the pressure cooker for a further 20 minutes, after which they are removed and rinsed. Proteinase antigen retrieval consists of a 4-minute incubation in protease-1 solution (Ventana) according to the supplier's recommended protocol.

In one embodiment, the present invention provides methods of treating a tumor in an animal with a chemotherapeutic regimen comprising:
(a) preparing a plurality of histologic sections of the tumor to obtain SPARC microenvironment signature,
(b) immunostaining a histologic section of the tumor with a first anti-SPARC antibody, wherein the first anti-SPARC antibody preferentially stains SPARC in tumor cells,
(c) immunostaining a histologic section of the tumor with a second anti-SPARC antibody, wherein the second anti-SPARC antibody preferentially stains SPARC in fibroblasts,
(d) determining the staining of the tumor cells, fibroblasts, inflammatory cells, acellular stroma/matrix, blood vessels, nerve tissue, normal anatomy within tumor or any combinations thereof with the first anti-SPARC antibody and the staining of the tumor cells, fibroblast, inflammatory cells, acellular stroma/matrix, blood vessels, nerve tissue, normal anatomy within tumor or any combinations thereof with the second antibody, and
(e) administering a therapeutically effective amount of the chemotherapeutic regimen if a predefined SMS is demonstrated by the immunostaining.

The invention provides several exemplary predefined SMS's for use in the method for treating a tumor in an animal with a chemotherapeutic regimen. One exemplary predefined SMS comprises immunostaining with at least 70% of tumor cells, fibroblasts, blood vessels, stroma and inflammatory cells staining positive with the first antibody and at least 50% of the inflammatory cells and at least 70% of the blood vessels, and stroma staining positive with the second antibody.

Another exemplary predefined SMS for use in the method for treating a tumor in an animal with a chemotherapeutic regimen comprises immunostaining with at least 60% of tumor cells, blood vessels, and stroma staining positive with the first antibody and at least 60% of the tumor cells staining positive with the second antibody.

Another exemplary predefined SMS for use in the method for treating a tumor in an animal with a chemotherapeutic regimen comprises immunostaining with less than 50% of tumor cells, blood vessels, and stroma staining positive with the first antibody and less than 50% of tumor cells, blood vessels, and stroma staining positive with the second antibody and blood vessels having at least a moderately positive score with the second antibody.

Another exemplary SMS for use in the method for treating a tumor in an animal with a chemotherapeutic regimen comprises immunostaining that has no more than 2+ intensity for the tumor cells, blood vessels, inflammatory cells and fibroblasts with the first antibody; no more than 50% of the tumor cells, blood vessels, inflammatory cells, stroma, and fibroblasts staining positive with the first antibody; and a score of no higher than a slightly positive with the first antibody for the tumor cells, blood vessels, inflammatory cells, stroma, and fibroblasts.

In preferred embodiments of the method for treating a tumor in an animal with a chemotherapeutic regimen the tumor is breast cancer and the predefined SMS comprises immunostaining with at least 70% of tumor cells, fibroblasts, blood vessels, stroma and inflammatory cells staining positive with first antibody and at least 50% of the inflammatory cells and at least 70% of the blood vessels, and stroma staining positive with the second antibody.

In another preferred embodiment of the method for treating a tumor in an animal with a chemotherapeutic regimen, the tumor is breast cancer and the predefined SMS comprises immunostaining with at least 60% of tumor cells, blood vessels, and stroma staining positive with the first antibody and at least 60% of the tumor cells staining positive with the second antibody. In a particularly preferred embodiment the tumor is a Her2 negative breast cancer and the chemotherapeutic regimen comprises preoperative therapy comprising 6 cycles of 14 days with nab-Paclitaxel (175 mg/m$^2$), gemcitabine (2000 mg/m$^2$), and epirubicin (50 mg/m$^2$) and postoperative therapy comprising (4 cycles of 14 days) and nab-Paclitaxel (220 mg/m$^2$)+gemcitabine (2000 mg/m$^2$).

In another particularly preferred embodiment of the method for treating a tumor in an animal with a chemotherapeutic regimen, the tumor is Her2 breast cancer, the predefined SMS comprises immunostaining with at least 60% of tumor cells, blood vessels, and stroma staining positive with the first antibody and at least 60% of the tumor cells staining positive with the second antibody, and the chemotherapeutic regimen comprises six cycles of (a) neoadjuvant nab-Paclitaxel at 125 mg/m2 on days 1, 8, 15 of each 28 day cycle; (b) carboplatin AUC6 on day 1 of each 28 day cycle (c) trastuzumab with a 4 mg/kg load followed by 2 mg/kg/week, and (d) bevacizumab at 5 mg/kg/week. The six cycles are then followed by surgical removal of the primary tumor, which is in turn followed by therapeutically effective amounts of trastuzumab and bevacizumab for 52 weeks.

In another preferred embodiment of the method for treating a tumor in an animal with a chemotherapeutic regimen, the tumor is pancreatic cancer the chemotherapeutic regimen comprises nab-Paclitaxel, and the predefined SMS comprises immunostaining with less than 50% of tumor cells, blood vessels, and stroma staining positive with the first antibody and less than 50% of tumor cells, blood vessels, and stroma staining positive with the second antibody and blood vessels having at least a moderately positive score with the second antibody.

In another preferred embodiment of the method for treating a tumor in an animal with a chemotherapeutic regimen, the tumor is melanoma, the chemotherapeutic regimen comprises nab-Paclitaxel, and the predefined SMS comprises immunostaining that has no more than 2+ intensity for the tumor cells, blood vessels, inflammatory cells and fibroblasts with the first antibody; no more than about 50% of the tumor cells, blood vessels, inflammatory cells, stroma, and fibroblasts staining positive with the first antibody; and a score of no higher than a slightly positive with the first antibody for the tumor cells, blood vessels, inflammatory cells, stroma, and fibroblasts.

In another embodiment, the invention provides a method for predicting the response of a tumor in an animal to a chemotherapeutic regimen comprising:
(a) preparing a plurality of histologic sections of the tumor to obtain SPARC microenvironment signature,
(b) immunostaining a histologic section of the tumor with a first anti-SPARC antibody, wherein the first anti-SPARC antibody preferentially stains SPARC in tumor cells,
(c) immunostaining a histologic section of the tumor with a second anti-SPARC antibody, wherein the second anti-SPARC antibody preferentially stains SPARC in fibroblasts,
(d) determining the staining of the tumor cells, fibroblasts, inflammatory cells, acellular stroma/matrix, blood vessels, nerve tissue, normal anatomy within tumor or any combinations thereof with the first anti-SPARC antibody and the staining of the tumor cells, fibroblast, inflammatory cells, acellular stroma/matrix, blood vessels, nerve tissue, normal anatomy within tumor or any combinations thereof with the second antibody, and
(e) predicting a positive response to the chemotherapeutic regimen if a predefined SMS is demonstrated by the immunostaining.

The invention also provides methods for predicting the response of a tumor in an animal to a chemotherapeutic regimen comprising: immunostaining a histologic section of the tumor with an anti-SPARC antibody that recognizes the immunodominant epitopes recognized by the AF941 polyclonal antibody, and predicting a positive response to the chemotherapeutic regimen if there is staining of the tumor cells in the histologic section with the anti-SPARC antibody. In particular, the invention provides methods for predicting the response of the tumor to chemotherapeutic regimen, wherein the chemotherapeutic regimen comprises administering an albumin bound nanoparticle paclitaxel and gemcitabine.

The invention also provides methods for predicting the response of a tumor in an animal to a chemotherapeutic regimen wherein "response" is defined as but not limited to pathological response, overall survival, or progression free survival. The method comprises: immunostaining a histologic section of the tumor with an anti-SPARC antibody, wherein the anti-SPARC antibody recognizes the epitope recognized by the MAB941 monoclonal antibody, and predicting a poor response to the chemotherapeutic regimen if there is staining of the tumor cells in the histologic section with the anti-SPARC antibody. In particular, the invention provides methods for predicting the response of a pancreatic carcinoma to chemotherapeutic regimen, wherein the chemotherapeutic regimen comprises administering an albumin bound nanoparticle paclitaxel and gemcitabine.

The invention provides several exemplary predefined SMS's for use in for predicting the response of a tumor in an animal to a chemotherapeutic regimen. One exemplary predefined SMS comprises immunostaining with at least 70% of tumor cells, fibroblasts, blood vessels, stroma and inflammatory cells staining positive with the first antibody and at least 50% of the inflammatory cells and at least 70% of the blood vessels, and stroma staining positive with the second antibody.

Another exemplary predefined SMS for use in the method for predicting the response of a tumor in an animal to a chemotherapeutic regimen comprises immunostaining with at least 60% of tumor cells, blood vessels, and stroma staining positive with the first antibody and at least 60% of the tumor cells staining positive with the second antibody.

Another exemplary predefined SMS for use in the method for predicting the response of a tumor in an animal to a chemotherapeutic regimen comprises immunostaining with less than 50% of tumor cells, blood vessels, and stroma staining positive with the first antibody and less than 50% of tumor cells, blood vessels, and stroma staining positive with the second antibody and blood vessels having at least a moderately positive score with the second antibody.

Another exemplary SMS for use in the method for predicting the response of a tumor in an animal to a chemotherapeutic regimen comprises immunostaining that has no more than 2+ intensity for the tumor cells, blood vessels, inflammatory cells and fibroblasts with the first antibody; no more than 50% of the tumor cells, blood vessels, inflammatory cells, stroma, and fibroblasts staining positive with the first antibody; and a score of no higher than a slightly positive with the first antibody for the tumor cells, blood vessels, inflammatory cells, stroma, and fibroblasts.

In another embodiment, the invention provides a method for predicting if an animal with a tumor has a low risk of the progression of that tumor comprising:
(a) Preparing a plurality of histologic sections of the tumor to obtain SPARC microenvironment signature,
(b) immunostaining a histologic section of the tumor with a first anti-SPARC antibody, wherein the first anti-SPARC antibody preferentially stains SPARC in tumor cells,
(c) immunostaining a histologic section of the tumor with a second anti-SPARC antibody, wherein the second anti-SPARC antibody preferentially stains SPARC in fibroblasts,
(d) determining the staining of the tumor cells, fibroblasts, inflammatory cells, acellular stroma/matrix, blood vessels, nerve tissue, normal anatomy within tumor or any combinations thereof with the first anti-SPARC antibody and the staining of the tumor cells, fibroblast, inflammatory cells, acellular stroma/matrix, blood vessels, nerve tissue, normal anatomy within tumor or any combinations thereof with the second antibody, and
(e) predicting a low risk of progression if a predefined SMS is demonstrated by the immunostaining.

The invention provides several exemplary predefined SMS's for use in predicting if an animal with a tumor has a low risk of the progression of that tumor. One such exemplary predefined SMS comprises immunostaining with less than 70% of tumor cells, fibroblasts, blood vessels, stroma and inflammatory cells staining positive with the first antibody and at least 50% of the inflammatory cells and at least 70% of the blood vessels, and stroma staining positive with the second antibody.

Another exemplary predefined SMS for use in the method for predicting if an animal with a tumor has a low risk of the progression of that tumor comprises immunostaining with at least 60% of tumor cells, blood vessels, and stroma staining positive with the first antibody and at least 60% of the tumor cells staining positive with the second antibody. In preferred embodiments, the tumor having this predefined SMS is a breast cancer tumor.

Another exemplary predefined SMS for use in the method for predicting if an animal with a tumor has a low risk of the progression of that tumor comprises immunostaining with less than 50% of tumor cells, blood vessels, and stroma staining positive with the first antibody and less than 50% of tumor cells, blood vessels, and stroma staining positive with the second antibody and blood vessels having at least a moderately positive score with the second antibody. In preferred embodiments, the tumor having this predefined SMS is a pancreatic cancer tumor.

Another exemplary SMS for use in the method for predicting if an animal with a tumor has a low risk of the progression of that tumor comprises immunostaining that has no more than 2+ intensity for the tumor cells, blood vessels, inflammatory cells and fibroblasts with the first antibody; no more than 50% of the tumor cells, blood vessels, inflammatory cells, stroma, and fibroblasts staining positive with the first antibody; and a score of no higher than a slightly positive with the first antibody for the tumor cells, blood vessels, inflammatory cells, stroma, and fibroblasts. In preferred embodiments, the tumor having this predefined SMS is a melanoma tumor.

A preferred embodiment of the method for predicting if an animal with a tumor has a low risk of the progression of that tumor wherein the tumor is breast cancer comprises a predefined SMS comprising immunostaining with less than about 70% of tumor cells, fibroblasts, blood vessels, stroma and inflammatory cells staining positive with first antibody and at least 50% of the inflammatory cells and at least 70% of the blood vessels, and stroma staining positive with the second antibody.

The method of predicting if an animal with a tumor has a low risk of the progression of that tumor may further comprise administering a chemotherapeutic regimen to the animal. In preferred embodiments, the chemotherapeutic regimen comprises paclitaxel.

In another embodiment, the invention provides a method for predicting if an animal with a tumor has a low risk of death from that tumor comprising:
(a) Preparing a plurality of histologic sections of the tumor to obtain SPARC microenvironment signature,
(b) immunostaining a histologic section of the tumor with a first anti-SPARC antibody, wherein the first anti-SPARC antibody preferentially stains SPARC in tumor cells,
(c) immunostaining a histologic section of the tumor with a second anti-SPARC antibody, wherein the second anti-SPARC antibody preferentially stains SPARC in fibroblasts,
(d) determining the staining of the tumor cells, fibroblasts, inflammatory cells, acellular stroma/matrix, blood vessels, nerve tissue, normal anatomy within tumor or any combinations thereof with the first anti-SPARC antibody and the staining of the tumor cells, fibroblast, inflammatory cells, acellular stroma/matrix, blood vessels, nerve tissue, normal anatomy within tumor or any combinations thereof with the second antibody, and
(e) predicting that the animal has a low risk of death from the tumor if a predefined SMS is demonstrated by the immunostaining.

The invention provides several exemplary predefined SMS's for use in predicting if an animal with a tumor has a low risk of death from that tumor. A preferred embodiment of the method for predicting if an animal with a tumor has a low risk of death from that tumor wherein the tumor is breast cancer comprises a predefined SMS comprising immunostaining with less than about 70% of tumor cells, fibroblasts, blood vessels, stroma and inflammatory cells staining positive with first antibody and at least 50% of the inflammatory cells and at least 70% of the blood vessels, and stroma staining positive with the second antibody.

Another preferred embodiment of the method for predicting if an animal with a tumor has a low risk of death from that tumor wherein the tumor is breast cancer comprises a predefined SMS comprising immunostaining with at least 60% of tumor cells, blood vessels, and stroma staining positive with the first antibody and at least 60% of the tumor cells staining positive with the second antibody.

Another preferred embodiment of the method for predicting if an animal with a tumor has a low risk of death from that tumor, wherein the tumor is pancreatic cancer, comprises a predefined SMS comprising immunostaining with less than 50% of tumor cells, blood vessels, and stroma staining positive with the first antibody and less than 50% of tumor cells, blood vessels, and stroma staining positive with the second antibody and blood vessels having at least a moderately positive score with the second antibody.

Another preferred embodiment of the method for predicting if an animal with a tumor has a low risk of death from that tumor, wherein the tumor is melanoma, comprises predefined SMS comprising immunostaining that has no more than 2+ intensity for the tumor cells, blood vessels, inflammatory cells and fibroblasts with the first antibody; no more than about 50% of the tumor cells, blood vessels, inflammatory cells, stroma, and fibroblasts staining positive with the first antibody; and a score of no higher than a slightly positive with the first antibody for the tumor cells, blood vessels, inflammatory cells, stroma, and fibroblasts.

The method of predicting if an animal with a tumor has a low risk of death from that tumor may further comprise administering a chemotherapeutic regimen to the animal. In preferred embodiments, the chemotherapeutic regimen comprises paclitaxel.

The invention also provides kits for predicting the response of a tumor in an animal to a chemotherapeutic regimen comprising:
(a) an immunostain with a first anti-SPARC antibody, wherein the first anti-SPARC antibody preferentially stains SPARC in tumor cells, and
(b) an immunostain with a second anti-SPARC antibody, wherein the second anti-SPARC antibody preferentially stains SPARC in fibroblasts.

The inventive methods include, without limitation, embodiments wherein the tumor is a tumor of a type such as oral cavity tumors, pharyngeal tumors, digestive system tumors, the respiratory system tumors, bone tumors, cartilaginous tumors, bone metastases, sarcomas, skin tumors, melanoma, breast tumors, the genital system tumors, urinary tract tumors, orbital tumors, brain and central nervous system tumors, gliomas, endocrine system tumors, thyroid tumors, esophageal tumors, gastric tumors, small intestinal tumors, colonic tumors, rectal tumors, anal tumors, liver tumors, gall bladder tumors, pancreatic tumors, laryngeal tumors, tumors of the lung, bronchial tumors, non-small cell lung carcinoma, small cell lung carcinoma, uterine cervical tumors, uterine corpus tumors, ovarian tumors, vulvar tumors, vaginal tumors, prostate tumors, prostatic carcinoma, testicular tumors, tumors of the penis, urinary bladder tumors, tumors of the kidney, tumors of the renal pelvis, tumors of the ureter, head and neck tumors, parathyroid cancer, Hodgkin's disease, Non-Hodgkin's lymphoma, multiple myeloma, leukemia, acute lymphocytic leukemia, chronic lymphocytic leukemia, acute myeloid leukemia, chronic myeloid leukemia and anal tumors.

In preferred embodiment of the invention, the tumor is breast cancer, pancreatic cancer, lung cancer or melanoma. In especially preferred embodiments, the tumor is breast cancer.

Any of the inventive methods include wherein the animal is a mammal. Even more preferably, the animal is a human.

The chemotherapeutic regimen to be used in the invention can be any appropriate regimen known to those skilled in the art. A preferred chemotherapeutic regimen will include treatment with paclitaxel. An even more preferred chemotherapeutic regimen will include treatment with nanoparticulate albumin bound paclitaxel. Further, one skilled in the are will know that a chemotherapeutic regimen may include combination therapy. Preferred combinations include, without limitation, nab-Paclitaxel, Gemcitabine and epirubicin; nab-paclitaxel and carboplatin; nab-paclitaxel and Trastuzumab; and nab-paclitaxel and Bevacizumab.

Particularly preferred chemotherapeutic regimens include any one of the following:
(a) neoadjuvant nab-Paclitaxel at 175 mg/m$^2$, Gemcitabine at 2000 mg/m$^2$, epirubicin at 50 mg/m$^2$ every 14 days for 6 cycles, followed by surgical removal of the primary tumor, followed by Post-surgery: nab-Paclitaxel at 220 mg/m$^2$ and Gemcitabine at 2000 mg/m$^2$ for 14 days for 4 cycles;
(b) nab-Paclitaxel (100-150 mg/m2) weekly for 3 consecutive weeks out of every 4 weeks and Gemcitabine (1000 mg/m2) weekly for 3 consecutive weeks out of every 4 weeks; or
(c) nab-Paclitaxel (100 mg/m2) weekly for 3 consecutive weeks out of every 4 weeks and Carboplatin (AUC 2) weekly for 3 consecutive weeks out of every 4 weeks.

Another preferred chemotherapeutic regimen comprises six cycles of:
(a) neoadjuvant nab-Paclitaxel at 125 mg/m2 on days 1, 8, 15 of each 28 day cycle; (b) carboplatin AUC6 on day 1 of each 28 day cycle (c) Trastuzumab with a 4 mg/kg load followed by 2 mg/kg/week, and (d) Bevacizumab at 5 mg/kg/week. The six cycles are then followed by surgical removal of the primary tumor, which is, in turn, followed by treatment with therapeutically effective amounts of Trastuzumab and Bevacizumab for 52 weeks.

The following examples further illustrate the invention but, of course, should not be construed as in any way limiting its scope.

Example 1

The purpose of this study was to evaluate which SPARC isoforms and functions in the tumor microenvironment are responsible for patient outcomes and, in particular, to determine if there were correlations between patterns of SPARC immunostaining and patient outcomes with a nanoparticulate albumin-bound (nab) paclitaxel (i.e., Abraxane®).

SPARC is a poor prognostic factor in multiple tumor types including breast, pancreatic, prostate, lung, melanoma, and head and neck cancers and has been associated with increased tumor angiogenesis, invasion and metastasis. nab-Paclitaxel can utilize endogenous pathways of albumin transport to enter tumor cells, including endothelial cell gp60-albumin receptor transport and binding to SPARC secreted by tumors. Initial preclinical studies and a small retrospective clinical study in head and neck cancer suggested that increased endogenous SPARC in tumor tissue may predict a favorable response to nab-paclitaxel treatment (Desai et al. 2009, Trans One. 2, 59-64).

Four prospective studies examined if SPARC tumor immunostaining patterns, i.e., the "SPARC microenvironment signatures" (SMS), could discriminate patients with low and high risks of recurrence when treated with nab-paclitaxel regimens.

The outcome of patients from the four clinical trials were evaluated (Table 1).

TABLE 1

Clinical Trials That Provided Specimens and Outcome Data

| Study | Indication | Phase | No. Pts | No. Pts with SPARC IHC | Regimen |
|---|---|---|---|---|---|
| N057E | Unresectable Stage IV Melanoma | II | 76 | 40 | nab-paclitaxel (100-150 mg/m$^2$) weekly for 3 consecutive weeks out of every 4 weeks carboplatin (AUC 2) weekly for 3 consecutive weeks out of every 4 weeks |
| CA040 | Metastatic Pancreatic Cancer | I/II | 63 | 37 | nab-paclitaxel (100-150 mg/m$^2$) weekly for 3 consecutive weeks out of every 4 weeks gemcitabine (1000 mg/m2) weekly for 3 consecutive weeks out of every 4 weeks |
| BRE73 | Neoadjuvant Breast Cancer | II | 123 | 83 | Preoperative: (6 cycles of 14 days) |

TABLE 1-continued

Clinical Trials That Provided Specimens and Outcome Data

| Study | Indication | Phase | No. Pts | No. Pts with SPARC IHC | Regimen |
|---|---|---|---|---|---|
| | (HER2−) | | | | nab-paclitaxel (175 mg/m$^2$) + gemcitabine (2000 mg/m2) + epirubicin (50 mg/m$^2$) Postoperative: (4 cycles of 14 days) nab-paclitaxel (220 mg/m$^2$) + gemcitabine (2000 mg/m$^2$) |
| BRE83 | Neoadjuvant Breast Cancer (HER2+) | II | 30 | 30 | Preoperative: (6 cycles of 28 days) nab-paclitaxel (100 mg/m$^2$) weekly for 3 consecutive weeks out of every 4 weeks + carboplatin (AUC6) + trastuzumab (4 mg/kg load, then 2 mg/kg/week) + bevacizumab (5 mg/kg/week) Post-operative maintenance (1 yr): trastuzumab (6 mg/kg) q3wk bevacizumab (15 mg/kg) q3wk |

Overall, this method is based on the consecutive application of (1) a primary antibody against the antigen to be localized, (2) biotinylated linking antibody, (3) enzyme-conjugated streptavidin, and (4) substrate chromagen (DAB). Slides are then counterstained in Richard-Allan hematoxylin (Kalamazoo, Mich.), dehydrated through graded ethanol solutions, and topped with a coverslip. All slides were stained using automated staining equipment (Dako Cytomation Autostainer, Dako, Carpinteria, Calif.).

The immunostaining in this example was performed as described below. A series of antibodies were evaluated against SPARC. Detailed immunohistologic evaluation was performed by a pathologist certified by the American Board of Pathology. Staining scores were assigned on scale of 0-4+, 4+ being the most positive. As it was not known which components of the tumor are important for SPARC's activity, a breakdown of the various components was performed, including staining in the tumor, blood vessels, fibroblasts, stromal cells, inflammatory cells, and the normal anatomy.

Tissue cores from formalin-fixed, paraffin-embedded tumor blocks (2 cores from the most representative areas per block) are arrayed (Beecher Instruments, Silver Spring, Md.) to create a tissue microarray of cores measuring 2.0 mm each and are placed on positively charged slides. Slides with specimens are placed in a 60° C. oven for 1 hour, cooled, deparaffinized, and rehydrated through xylenes and graded ethanol solutions to water. All slides are quenched for 5 minutes in a 3% hydrogen peroxide solution in water to block for endogenous peroxidase.

Antigen retrieval is performed if no staining is seen and with the staining of normal tissue in the same field serving as an internal positive control. Antigen retrieval is performed by a heat method in which the specimens are placed in a citric acid solution, pH 6.1 (code S1699, Dako, Carpinteria, Calif.) for 20 minutes at 94° C. using a vegetable steamer, then cooled for 15 minutes. Slides are then placed on an immunostaining system such as the Dako Cytomation Autostainer (Dako, Carpinteria, Calif.) for use with immunohistochemistry utilizing suitable antibodies.

Two antibodies with differential affinity for SPARC were identified for this study, a monoclonal antibody (indicated hereinafter by "M") (SPARC monoclonal antibody (R&D Systems, Minneapolis, Minn.), catalog #MAB941 Lot # ECH045011 diluted 1:100 in a tris based diluent) and a polyclonal antibody (indicated hereinafter by "P") (SPARC polyclonal antibody (R&D Systems, Minneapolis, Minn.), catalog #AF941 Lot # EWN04 diluted 1:50 in a tris based diluents). Histologic sections of tumors were prepared on slides and stained using a standard immunostaining protocol. All slides were quenched for 5 minutes in a 3% hydrogen peroxide solution in water to block for endogenous peroxidase. After a buffer rinse, slides were incubated with antibody M or a negative control reagent for 30 minutes. A mouse horseradish peroxidase polymer kit (Mouse MACH 3 HRP Polymer Kit, Biocare Medical, Concord, Calif.) was incubated for 20 minutes per reagent. After another buffer rinse, DAB chromagen (Dako, Carpinteria, Calif.) was applied for 10 minutes. Hematoxylin was used to counterstain the slides. The same protocol was used for immunostaining specimens with antibody P, although an avidin-biotin detection kit (Biocare Medical, Concord, Calif.), incubated for 15 minutes per reagent, was used in place of the HRP detection kit.

Detailed pathological evaluation of SPARC expression in a series of tumors was performed by a board certified pathologist. The level of SPARC expression, as determined by immunohistochemistry, was scored for different tumor components. Scores were assigned to the level of SPARC expression on scale of 0-3, with 3 being the most positive score, as is commonly done in the art and well known to those of ordinary skill in the art. The monoclonal and polyclonal antibodies used detected different patterns of SPARC expression as shown in Table 2.

TABLE 2

M and P Immunostaining Profiles.

| | Tumor | | | Fibroblast | | |
|---|---|---|---|---|---|---|
| | Antibody P | Antibody M | | Antibody P | Antibody M | |
| Breast | 30/106 | 35/106 | p = ns | 82/107 | 26/107 | p < 0.0001 |
| Pancreas | 20/36 | 7/36 | p = 0.0031 | 18/29 | 5/29 | p = 0.0011 |
| Melanoma | 30/41 | 20/41 | p = 0.0408 | 19/33 | 14/33 | p = ns |

The polyclonal antibody demonstrated preferential staining of fibroblast associated SPARC, while the monoclonal anybody preferential stained tumor associated SPARC.

From these staining preferences the following patterns (designated A through E) were established and analyzed for their predictive value in a series of tumors:

A: when 3+ was found in any of the components.
B: when 3+ was found in any of the components with the monoclonal anti-SPARC antibody.
C: when 3+ was found in any of the components with the polyclonal anti-SPARC antibody.
D: when 3+ was found in tumor cells with both anti-SPARC antibodies.
E: when 3+ was found in fibroblasts with both anti-SPARC antibodies.

Logistic regression and proportional hazard were used to identify any correlations between SMS and response, progression free survival (PFS), and overall survival (OS) to SPARC staining pattern in various tumors. The following were eliminated from statistical analysis due to insufficient sample size as a large number of tissue samples did not contain these structures: inflammatory cells, blood vessels, nerve cells, stroma, normal tissue anatomy One of the tumor sets was a phase II trial of carboplatin and nab-paclitaxel (ABI-007) in patients with unresectable stage 1V melanoma (the N057E study listed above). nab-paclitaxel (100 mg/m$^2$) and Carboplatin (AUC2) were administered on days 1, 8, and 15 of a 28 day cycle. There was a statistically significant correlation between the presence of pattern "D" and overall survival.

Another set of tumors, from patients with advanced pancreatic adenocarcinoma who had been treated with Abraxane doses (100-150 mg/m$^2$) and Gencitabine (1000 mg/m$^2$) administered on days 1, 8, and 15 of a 28-day cycle (the CA040 study listed above). Among these patients following responses were observed:

TABLE 3

Response Rates

| Response | CR | PR | SD | PD |
|---|---|---|---|---|
| N of 32 pts | 2 (6%) | 14 (44%) | 14 (44%) | 2 (6%) |

(*CR, Complete Response; PR, Partial Response; SD, No Response and Stable Disease; PD, No Response and Progressive Disease)

Staining of the tumor with the polyclonal antibody was predictive of responsiveness to therapy in this second set of tumors (advanced pancreatic cancer) (one tail t-test, p=0.027). In addition, staining of the tumor cells with the monoclonal antibody predicted a worse overall survival and progression free survival. Further, B pattern staining was predictive of the worst progression free survival with this regimen in these patients with pancreatic adenocarcinoma.

This Example demonstrates that SPARC immunohistochemistry is a fruitful method for predicting response to nab-paclitaxel based chemotherapies.

Example 2

A more systematic analysis of the staining pattern data from SPARC immunostaining was undertaken to identify patterns which produced prognostic information, Staining pattern data from the same tumor sets studied in Example 1 were mined using various forms of cluster analysis to identify the most distinguishing components of SPARC expression (as indicated by the immunostaining pattern) for response, progression free survival (PFS), and overall survival (OS) to SPARC staining pattern in various tumors. As noted above, the patterns which emerged as prognostically significant are referred to as "SPARC microenvironment signatures" ("SMS").

SPARC expression in seven tumor components taken from samples obtained in the studies described above was characterized via immunostaining with two different antibodies, M and P (see Example 1). These tumor components were tumor cells, fibroblasts, inflammatory cells, acellular stroma/matrix (stroma), blood vessels, nerves and the other normal anatomy within the tumor. The percent of cells stained in each field, the intensity of staining (0-4) and an overall score (dependant variable) for each of the components of the tumor were determined (total variables per patient: 7 components×2 antibodies×3 scores=42 variables scored.).

The scoring combined the percent positive cells and staining intensity. The score was negative if no cells or none of the component stained positive. The score was "weakly positive" if <10% of the cells were positive, the intensity was 2+ or less and <20% of the cells were positive, or the intensity was 1+ or less and <30% of the cells were positive. The score was "moderately positive" if the intensity was 4+ and 10-40% of the cells were positive, the intensity was 3+ and 10-50% of the cells were positive, the intensity was 2+ and 20-70% of the cells were positive, or the intensity was 4+ or less and 20-40% of the cells were positive or the intensity was 1+ or less and >30% of the cells were positive. The score was "strongly positive" if the intensity was 4+ and >40% of the cells were positive, or the intensity was 3+ and >50% of the cells were positive, the intensity was 2+ and >70% of the cells were positive. This system is summarized in Table 4.

TABLE 4

SMS Scoring System

| % positive for SPARC | Intensity of SPARC staining | | | | |
|---|---|---|---|---|---|
| | 0+ | 1+ | 2+ | 3+ | 4+ |
| 0 | Negative | Weak | Weak | Weak | Weak |
| 10 | Negative | Weak | Weak | Moderate | Moderate |
| 20 | Negative | Weak | Moderate | Moderate | Moderate |
| 30 | Negative | Moderate | Moderate | Moderate | Moderate |
| 40 | Negative | Moderate | Moderate | Moderate | Strong |
| 50 | Negative | Moderate | Moderate | Strong | Strong |
| 60 | Negative | Moderate | Moderate | Strong | Strong |
| 70 | Negative | Moderate | Strong | Strong | Strong |
| 80 | Negative | Moderate | Strong | Strong | Strong |
| 90 | Negative | Moderate | Strong | Strong | Strong |

This data was mined using the clustering programs in the GeneSpring software suite and Nexus array analysis programs. In addition, ANOVA or t-test (unpaired) statistics were determined for parameters that clustering suggested to have discriminating power for various outcome parameters. For analysis in clustering programs the immunostaining results are normalized to 0+=0, 1+=25, 2+=50, 3+=75, 4+=100, negative=0, weak=33, moderate=66, strong=100, and % is the % reported by the pathologist. Using this protocol the SMS components which provide statistically significant prognostic information can be identified for any tumor/therapy combination. Exemplary results for breast carcinoma, melanoma and pancreatic carcinoma are shown in Tables 5-7.

TABLE 5

Breast Cancer SMS components which provide statistically significant prognostic information. (Hierarchical Clustering, BRE73 Study, 38 high risk, 30 low risk patients, overall survival).

| SMS Component | SPARC High Risk | SPARC Low Risk | High vs Low Risk cluster p-value |
|---|---|---|---|
| P Tumor % | 79.80 | 47.50 | 5.89E−08 |
| P Inflammatory Cells Score | 72.96 | 51.58 | 5.11E−06 |
| P Fibroblast Intensity | 86.02 | 66.67 | 5.48E−06 |
| M Inflammatory Cells Score | 75.82 | 54.20 | 2.03E−05 |
| P Blood Vessel Score | 68.29 | 48.83 | 2.99E−05 |
| P Inflammatory Cells Intensity | 87.70 | 71.22 | 4.92E−05 |
| M Fibroblast Score | 44.24 | 28.24 | 1.47E−04 |
| P Tumor Score | 73.24 | 55.70 | 2.90E−04 |
| P Blood Vessel % | 82.11 | 67.82 | 3.06E−04 |
| P Stroma % | 64.87 | 49.67 | 1.19E−03 |
| P Fibroblast Score | 80.79 | 64.33 | 1.36E−03 |
| M Fibroblast % | 90.83 | 80.73 | 1.75E−03 |
| P Stroma Score | 62.50 | 46.67 | 1.76E−03 |
| M Stroma Score | 67.41 | 56.73 | 2.77E−03 |
| P Fibroblast % | 62.59 | 50.22 | 6.10E−03 |
| M Blood Vessel Intensity | 69.21 | 55.33 | 6.42E−03 |
| P Stroma Intensity | 40.80 | 29.67 | 7.05E−03 |
| M Blood Vessel Score | 32.41 | 25.90 | 1.31E−02 |
| M Stroma % | 68.33 | 58.45 | 1.88E−02 |
| M Inflammatory Cells Intensity | 79.08 | 66.67 | 2.20E−02 |
| P Inflammatory Cells % | 34.87 | 27.62 | 3.46E−02 |
| M Tumor Intensity | 58.82 | 48.00 | 4.17E−02 |

TABLE 6

Melanoma SMS components which provide statistically significant prognostic information. (Hierarchical Clustering, ABX054 study, 31 high risk, 9 low risk patients, overall survival).

| SMS Component | SPARC High Risk | SPARC Low Risk | High vs Low Risk cluster p-value |
|---|---|---|---|
| M Blood Vessel Score | 71.85 | 29.44 | 5.51E−08 |
| M Tumor Score | 85.77 | 47.89 | 4.14E−05 |
| M Blood Vessel % | 55.65 | 22.50 | 3.40E−04 |
| M Tumor % | 75.16 | 46.11 | 5.31E−04 |
| M Inflammatory Cells Score | 67.32 | 35.00 | 6.94E−04 |
| M Fibroblast Score | 79.79 | 49.72 | 6.95E−04 |
| M Tumor Intensity | 44.35 | 25.11 | 2.78E−03 |
| M Blood Vessel Intensity | 35.48 | 22.33 | 5.27E−03 |
| M Stroma Score | 58.02 | 42.17 | 5.31E−03 |
| M Inflammatory Cells % | 53.23 | 28.06 | 6.78E−03 |
| P Blood Vessel Intensity | 32.26 | 47.22 | 1.10E−02 |
| M Fibroblast % | 69.92 | 48.33 | 1.31E−02 |
| M Stroma % | 48.31 | 26.11 | 1.54E−02 |
| M Fibroblast Intensity | 41.53 | 29.17 | 2.11E−02 |
| M Inflammatory Cells Intensity | 33.87 | 23.72 | 2.69E−02 |
| P Blood Vessel Score | 65.10 | 81.11 | 3.89E−02 |
| P Tumor Score | 86.87 | 100.00 | 4.57E−02 |

TABLE 7

Pancreatic Carcinoma SMS components which provide statistically significant prognostic information. (Hierarchical Clustering, CA040 Study, 16 high risk, 20 low risk patients, overall survival).

| SMS Component | SPARC High Risk | SPARC Low Risk | High vs Low Risk cluster p-value |
|---|---|---|---|
| Poly Fibroblast Score | 66.52 | 86.83 | 1.01E−06 |
| Poly Fibroblast Intensity | 40.63 | 67.81 | 1.57E−04 |
| Poly Tumor Intensity | 25.84 | 48.80 | 2.27E−04 |
| Mab Stroma % | 61.88 | 82.00 | 3.28E−03 |
| Poly Inflammatory Cells Intensity | 25.84 | 42.26 | 4.29E−03 |
| Poly Inflammatory Cells Score | 49.05 | 67.14 | 7.49E−03 |
| Poly Blood Vessel % | 50.94 | 68.00 | 8.09E−03 |
| Poly Tum or Score | 54.72 | 75.55 | 8.10E−03 |
| Poly Blood Vessel Intensity | 32.81 | 45.96 | 9.44E−03 |
| Poly Fibroblast % | 54.06 | 70.63 | 1.37E−02 |
| Poly Blood Vessel Intensity | 63.52 | 75.03 | 2.02E−02 |
| Poly Inflammatory Cells % | 42.66 | 58.50 | 2.81E−02 |
| Poly Stroma Score | 61.88 | 50.55 | 5.00E−02 |

Although any one of the SPARC SMS components identified in Tables 5-7 can be used to predict the response of the particular tumor studied to the particular therapy studied, the use of the combination of many or all of the SPARC SMS components identified in the Table corresponding to a particular tumor and a particular therapy offer a substantially more accurate prediction of the response of the particular tumor to the particular therapy. Accordingly, the sum of the normalized scores for all of the components in a table for a given tumor/therapy pair can be used to classify a patient as high or low risk. Cut off values would be those shown in Tables 5-7 or the column sums.

Among the SMS identified were immunostaining with at least 70% of tumor cells, fibroblasts, blood vessels, stroma and inflammatory cells staining positive with first antibody and at least 50% of the inflammatory cells and at least 70% of the blood vessels, and stroma staining positive with the second antibody. Another SMS comprises immunostaining with less than 50% of tumor cells, blood vessels, and stroma staining positive with the first antibody and less than 50% of tumor cells, blood vessels, and stroma staining positive with the second antibody and blood vessels having at least a moderately positive score with the second antibody. Another SMS has immunostaining that has no more than 2+ intensity for the tumor cells, blood vessels, inflammatory cells and fibroblasts with the first antibody; no more than 50% of the tumor cells, blood vessels, inflammatory cells, stroma, and fibroblasts staining positive with the first antibody; and a score of no higher than a slightly positive with the first antibody for the tumor cells, blood vessels, inflammatory cells, stroma, and fibroblasts.

Example 3

In this Example the SMS of breast tumors was correlated with clinical outcomes.

One hundred twenty three patients with locally advanced breast cancer (LABC) were treated with 6 cycles of Gemcitabine 2000 mg/m$^2$, Epirubicin 50 mg/m$^2$, and nab-Paclitaxel 175 mg/m2 q14 days followed by surgery (see FIG. 1). After surgery the patients received 4 cycles of Gemcitabine 2000 mg/m$^2$ and nab-P 220 mg/m$^2$ q14 days (see FIG. 1). "Pathologic complete response" (pCR) was defined as the absence of residual invasive cancer in the breast (pT0) and axillary lymph nodes (pN0). "Complete response" (CR) was defined as pathological complete response in the breast only.

SPARC Immunohistochemistry (IHC) component scoring was performed on pretreatment tumor samples. SPARC immunostaining in tumor biopsies was scored independently by 2 board certified pathologists using a validated IHC protocol in accordance with the invention that quantifies SPARC expression with 2 different antibodies (Antibody M and P) for 7 tumor components: tumor cells, fibroblast, inflammatory cells, acellular stroma/matrix, blood vessels, nerve tissue, normal tissue within tumor. This scoring included a determination of the percent cells stained in each field, the intensity of staining, and an overall score (dependent variable). Thus, 42 variables were determined per patient (7 components, 2 antibodies and 3 scores). Analyses/clustering of data (SOM, Hierarchical, K-means, and the link) was performed using Partek array analysis programs. Metrics of success such as, e.g., progression free survival (PFS) were correlated with SMS using standard statistical methods.

SPARC IHC data was generated for 76 patients, with 18/76 (24%) having progression or death. (Surprisingly patients with higher SPARC fared better—while not desiring to be bound by an particular theory, these data suggest targeting by nab-paclitaxel.)

Based upon cluster analysis unique SMS's were identified that distinguished a low risk (LR) group (n=35, PFS 81% at 24 mos) from a high risk (HR) group (n=41, PFS 65% at 24 mos), p=0.02. There were 3 patients with pCR in the LR group and 5 pCR in the HR group (p=ns). The TN stage, triple-negative status, ER (estrogen receptor) status, and PR (progesterone receptor) status were similar between the 2 groups.

TABLE 7

|  | ER-neg (N = 31) | PR-neg (N = 35) | Triple-neg (N = 26) |
| --- | --- | --- | --- |
| # SPARC HR tumors with prognostic factors | 13/30 (43%) | 15/30 (50%) | 11/30 (37%) |
| # SPARC LR tumors with prognostic factors | 18/38 (47%) | 20/38 (53%) | 15/38 (39%) |
| Statistics (Chi²) | p = ns | p = ns | p = ns |

The prognostic power of SPARC SMS was improved by combining it with TN, ER−, PR−. For example, PFS at 24 months was 93% (n=24, non-TN, SPARC LR), 93% (n=21, ER+, SPARC LR), and 92% (n=20, PR+, SPARC LR) versus 33% (n=15, TN, SPARC HR), 40% (n=20, ER−, SPARC HR), and 51% (n=22, PR−, SPARC HR), p<0.0001, p=0.0001, p=0.002, respectively. Median PFS decreased from 22.7, 30.0, and 22.7 months for TN, ER−, PR− to 19.5, 24.2, and 14.3 months when HR SMS was combined with TN, ER−, and PR−.

Figure 3:
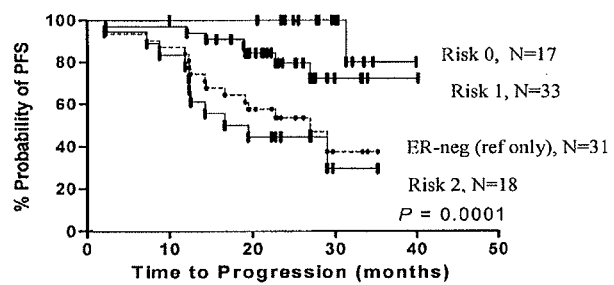
Figure 3:
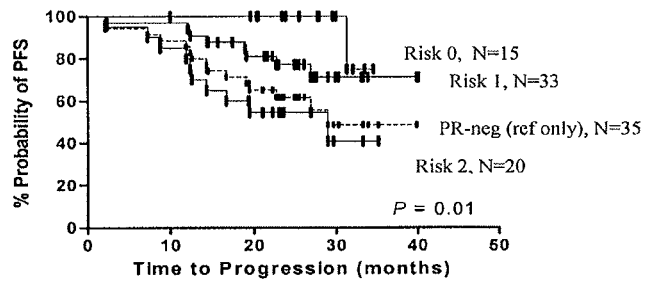
Figure 3:
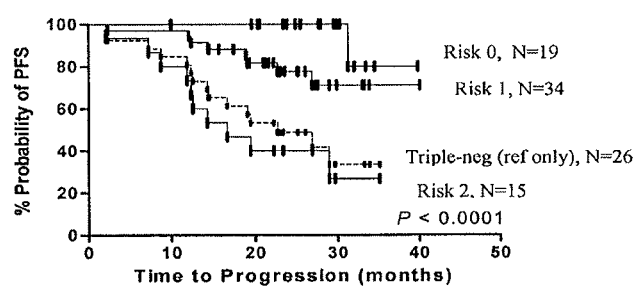
Figure 4:
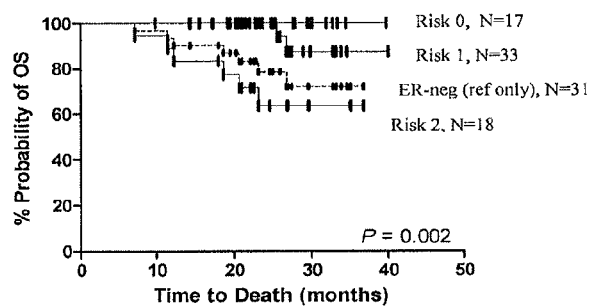
Figure 4:
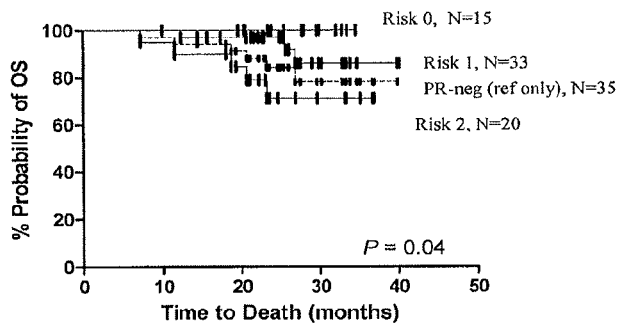
Figure 4:
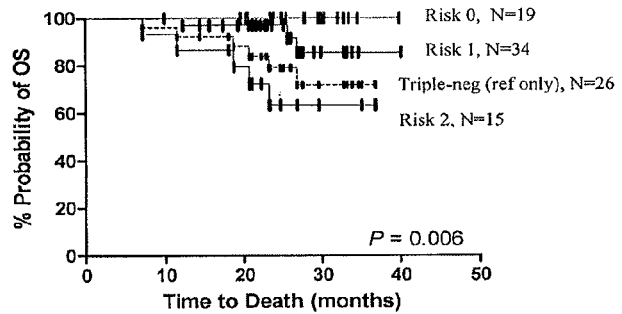

Overall PFS and OS with HER2-negative patients in the neoadjuvant breast cancer trial (N=107) are shown in FIGS. 3 and 4. (Median PFS and OS have not been reached for this patient population.) Tumor responses (CR and pCR) showed a trend towards better PFS and OS but were not statistically significant. The SPARC SMS from 68 of these HER2-negative patients correlated with PFS and survival.

TABLE 8

| Best Response | HER2-negative Pts (N = 107) | | HER2-neg Pts with SPARC data (N = 68) | |
| --- | --- | --- | --- | --- |
|  | # Pts | % Pts | # Pts | % Pts |
| pCR | 20 | 18.7% | 11 | 16.2% |
| CR | 6 | 5.6% | 4 | 1.5% |
| PR | 67 | 62.6% | 40 | 58.8% |
| SD | 7 | 6.5% | 7 | 10.3% |
| PD | 2 | 1.9% | 2 | 2.9% |
| UE | 5 | 4.7% | 4 | 5.9% |

The status of known prognostic factors (ER, PR, and triple negative) were investigated by IHC and correlated with PFS and OS in the 68 HER2-negative patients with available SPARC SMS data (Log rank test). The prognostic factors stratified patients as expected with significant P values with respect to PFS and OS.

SPARC as a prognostic factor is independent of ER, PR and triple negative tumor status. The addition of SMS risk clusters to other prognostic factors further discriminated tumors with low risk (0 risk factor), medium risk (1 risk factor), and high risk (2 risk factors) with regard to shortened PFS. (Risk 0: SPARC LR, and no known risk factor; Risk 1: SPARC HR, or ER-neg (A), PR-neg (B), Triple-neg (C); Risk 2: SPARC HR plus the known risk factor.) (FIG. 5). Addition of SMS risk clusters to other prognostic factors further discriminated tumors with low risk (0 risk factor), medium risk (1 risk factor), and high risk (2 risk factors) with regard to shortened OS (FIG. 6).

Thus, this Example shows that the SPARC microenvironment signature alone can discriminate between Low Risk and High Risk tumors with respect to OS.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a human patient with a breast tumor exhibiting a SPARC microenvironment signature comprising:
   (a) preparing a plurality of histological sections of the tumor to obtain a SPARC microenvironment signature by immunostaining a histological sections of the tumor with a first anti-SPARC antibody, wherein the first anti-SPARC antibody binds to the immunodominant epitopes bound by the anti-SPARC polyclonal antisera AF941, and immunostaining histological sections of the tumor with a second anti-SPARC antibody, wherein the second anti-SPARC antibody binds to the epitope bound by the anti-SPARC monoclonal antibody Mab941;
   (b) selecting a patient with a breast tumor having a SPARC microenvironment signature of least 70% of the tumor cells, fibroblasts, blood vessels, stroma and inflammatory cells staining positive with the first antibody, and at least 50% of the inflammatory cells and at least 70% of the blood vessels and stroma staining positive with the second antibody; and
   (c) administering a therapeutically effective amount of a chemotherapeutic regimen to the selected patient.

2. A method of treating a human patient with a breast tumor exhibiting a SPARC microenvironment signature comprising:
   (a) preparing a plurality of histological sections of the tumor to obtain a SPARC microenvironment signature by immunostaining a histological sections of the tumor with a first anti-SPARC antibody, wherein the first anti-SPARC antibody binds to the immunodominant epitopes bound by the anti-SPARC polyclonal antisera AF941, and immunostaining histological sections of the tumor with a second anti-SPARC antibody, wherein the second anti-SPARC antibody binds to the epitope bound by the anti-SPARC monoclonal antibody Mab941;
   (b) selecting a patient with a breast tumor having a SPARC microenvironment signature of least 60% of the tumor cells, blood vessels, and stroma staining positive with the first antibody, and at least 60% of the tumor cells staining positive with the second antibody; and
   (c) administering a therapeutically effective amount of a chemotherapeutic regimen to the selected patient.

3. The method of claim 1 or 2, wherein the tumor is a Her2 positive breast cancer and wherein the chemotherapeutic regimen comprises six cycles of:
   (a) neoadjuvant nab-paclitaxel at 125 mg/m2 on days 1, 8, 15 of each 28 day cycle,
   (b) carboplatin AUC6 on day, 1 of each 28 day cycle,
   (c) trastuzumab with a 4 mg/kg load followed by 2 mg/kg/week, and
   (d) bevacizumab at 5 mg/kg/week,
   followed by surgical removal of the primary tumor,
   followed by therapeutically effective amounts of trastuzumab and
   bevacizumab for 52 weeks.

4. The method of claim 1 or 2, wherein the tumor is a Her2 negative breast cancer and wherein the chemotherapeutic regimen comprises
   (a) preoperative therapy comprising 6 cycles of 14 days with nab-paclitaxel (175 mg/m$^2$), gemcitabine (2000 mg/m$^2$), and epirubicin (50 mg/m$^2$) and
   (b) postoperative therapy comprising 4 cycles of 14 days with nab-paclitaxel (220 mg/m$^2$) and gemcitabine (2000 mg/m$^2$).

5. The method of claim 1, wherein the first anti-SPARC antibody is the polyclonal antisera AF91 and the second anti-SPARC antibody, is the monoclonal antibody Mab 941.

6. The method of claim 2, wherein the first anti-SPARC antibody is the polyclonal antisera AF91 and the second anti-SPARC antibody, is the monoclonal antibody Mab 941.

* * * * *